United States Patent [19]
Failla et al.

[11] Patent Number: 5,364,410
[45] Date of Patent: Nov. 15, 1994

[54] PERCUTANEOUS SUTURE EXTERNALIZER

[75] Inventors: Stephen J. Failla; Charles M. Rarey; Michael J. Stokes, all of Cincinnati, Ohio

[73] Assignee: Ethicon, Inc., Cincinnati, Ohio

[21] Appl. No.: 74,321

[22] Filed: May 28, 1993

[51] Int. Cl.$^5$ ............................................. A61B 17/00
[52] U.S. Cl. ..................................... 606/148; 606/135; 606/139
[58] Field of Search ................ 606/148, 139, 144, 145, 606/146, 147, 113, 108-135

[56] References Cited

U.S. PATENT DOCUMENTS

| | | |
|---|---|---|
| 3,877,434 | 4/1975 | Ferguson et al. ............... 606/148 X |
| 4,372,302 | 2/1983 | Åkerlund ........................ 606/148 X |
| 5,015,250 | 5/1991 | Foster ............................. 606/148 X |
| 5,144,961 | 9/1992 | Chen et al. ..................... 606/148 X |
| 5,234,439 | 8/1993 | Wilk ................................ 606/113 X |
| 5,250,054 | 10/1993 | Li ..................................... 606/148 |
| 5,256,148 | 10/1993 | Smith et al. .................... 604/158 |

FOREIGN PATENT DOCUMENTS 1389761  4/1988  U.S.S.R. ........................... 606/148

Primary Examiner—Peter A. Aschenbrenner
Attorney, Agent, or Firm—Dressler, Goldsmith, Shore & Milnamow, Ltd.

[57] ABSTRACT

Percutaneous suture externalizer devices are disclosed which grasp, secure and externalize sutures from within an abdominal or thoracic cavity. The suture externalizer devices include a thin tubular sheath with a penetrating point and a hook rod slidable within the sheath. The hook rod is slidable between an extended position and a retracted position. The hook rod is biased to the extended position. In the retracted position, a suture grasped within the hook is snugly held between the hook rod and the inner wall of the sheath, providing a positive means of securing the suture during externalization. An alternative embodiment utilizes a hollow tubular hook rod that can also be used to insufflate the abdominal or thoracic cavity. The alternative embodiment utilizes a valve to control the flow of gas through the hook rod, into and out of the cavity.

19 Claims, 3 Drawing Sheets

U.S. Patent     Nov. 15, 1994     Sheet 1 of 3     5,364,410
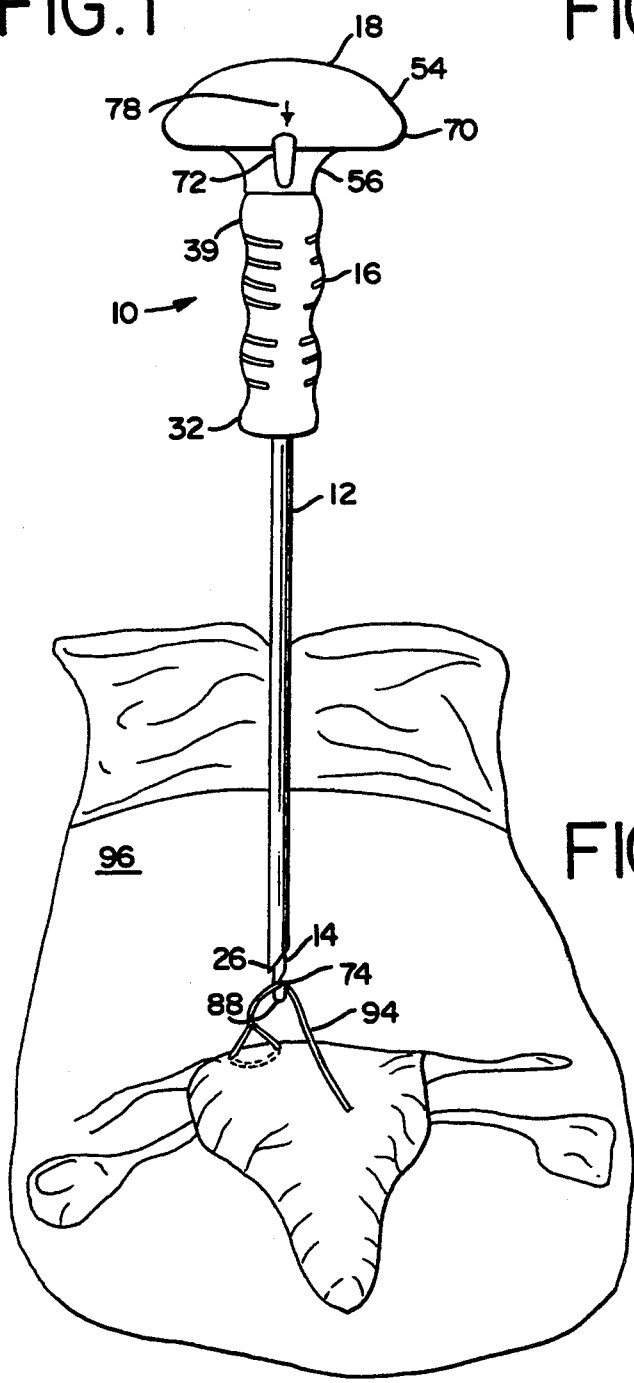
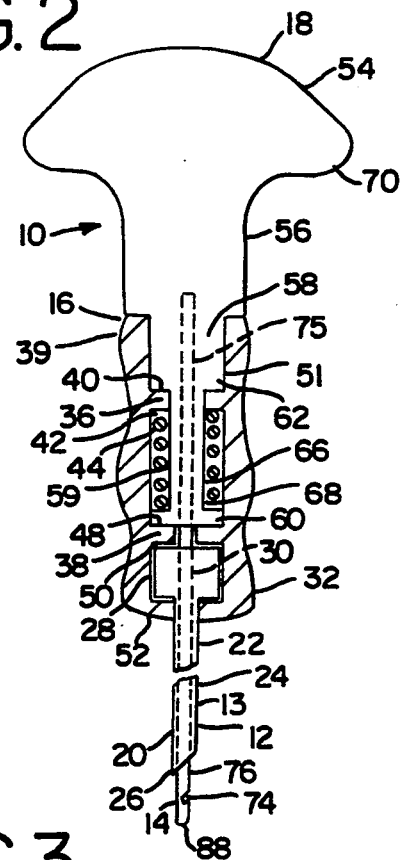
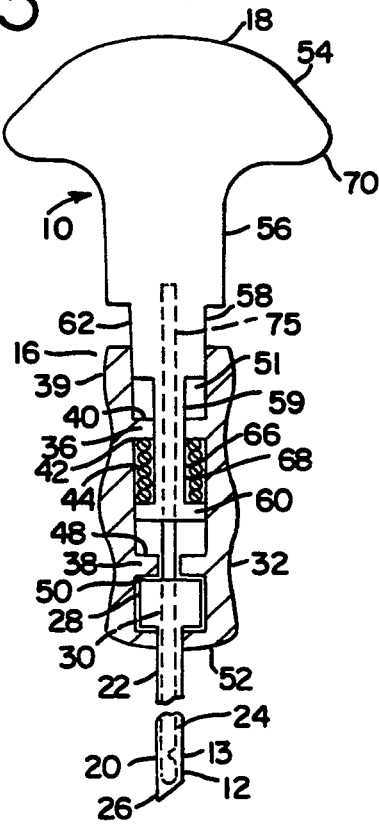

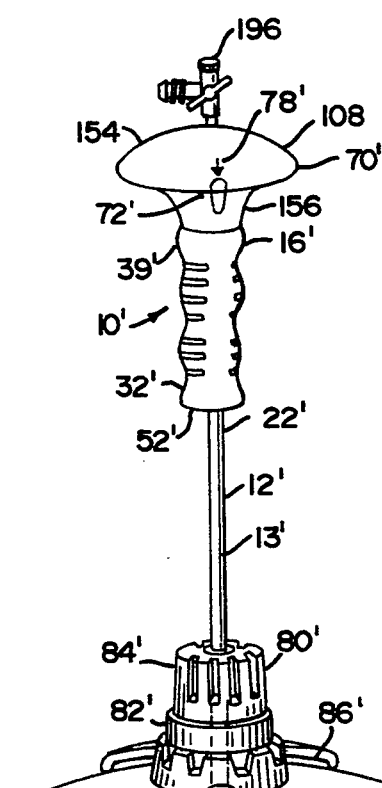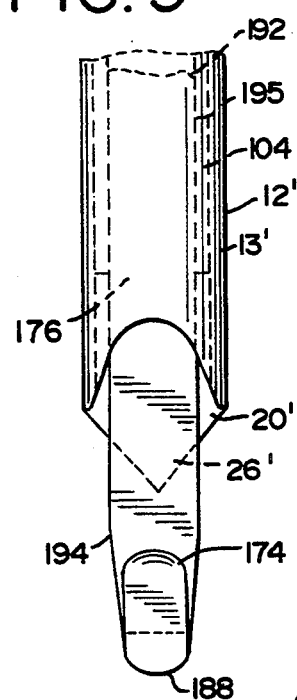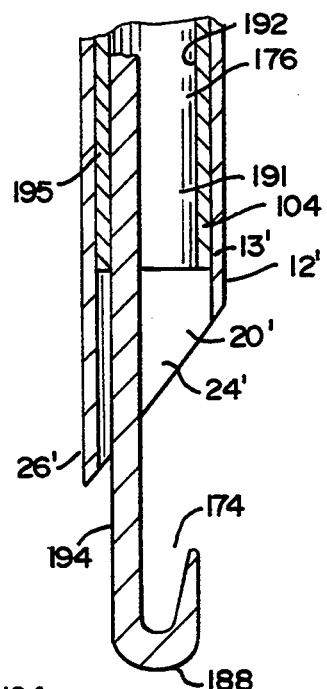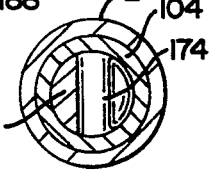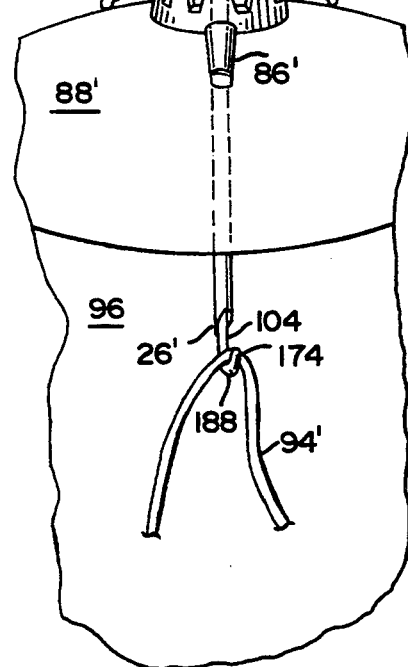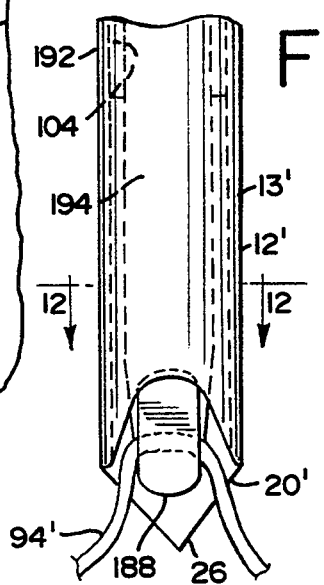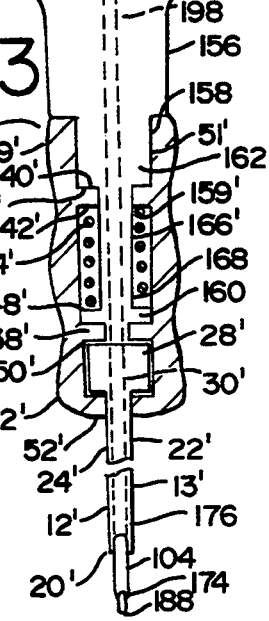

PERCUTANEOUS SUTURE EXTERNALIZER

FIELD OF THE INVENTION

This invention generally relates to surgical instruments; and more particularly, the invention relates to suture externalizing devices for grasping, securing and externalizing sutures from within the abdominal or thoracic cavity.

BACKGROUND OF THE INVENTION

Semm Emergency Needles are commonly known in the surgical instruments art. Semm Needles are used to externalize sutures from within the abdominal cavity. The Semm Needle is a reusable, exposed crochet type hooked needle mounted to a rod, the rod being approximately 3 millimeters in diameter. In use, the Semm Needle requires excessive force to penetrate the peritoneum. This excessive force tends to minimize control of the Semm Needle during penetration. Thus, once the peritoneum is penetrated, the Semm Needle tends to plunge into the abdominal cavity with minimal control.

An additional disadvantage of the Semm Needle is that once it penetrates the peritoneum, the sharp needle point remains exposed. The exposed point increases the potential for damage due to inadvertently perforating organs or tissue.

Another disadvantage of the Semm Needle is that it lacks a means to positively secure a suture portion once it is grasped within the hook. Using a Semm Needle, a suture may tend to dislodge from the hook during externalization because the suture is not securely held within the device. A further disadvantage of the Semm Needle is that upon removal from the abdominal cavity it can damage the surrounding tissue.

Veress needles are commonly known in the surgical instruments art. Veress needles are used to insufflate the abdominal cavity using compressed gas. A Veress needle includes an inner dull stylet slidably mounted in a sheath. The sheath of a Veress needle has a sharp outer point for penetrating tissue. The inner dull stylet is spring biased such that it retracts during penetration and extends once it is beyond the resistant tissue. Veress needles, however, do not provide a means or mechanism for securing and externalizing sutures.

SUMMARY OF THE INVENTION

In accordance with the principles of the present invention, percutaneous suture externalizing devices are provided that include a sheath of varying length with a penetrating point located at the distal end. The outside diameter of the sheath is sufficiently small such that the penetration location is self-sealing without sutures.

The sheath accommodates a slidable hook rod to grasp and secure sutures internal to the abdominal or thoracic cavity. A hook is located in the distal portion of the hook rod. The distal portion of the hook rod has a smaller diameter than the proximal portion, preferably being tapered inwardly and distally. The taper allows the sheath to accommodate both the hook rod and the portion of suture grasped therein to facilitate withdrawal of the suture from the abdominal or thoracic cavity.

The invention contemplates utilizing a biasing means to selectively move the hook rod within the sheath. In a first or extended position, the distal portion of the hook rod is extended beyond the penetrating point of the sheath. When a force is applied against the biasing means toward a second or retracted position, the hook rod is retracted within the sheath. The suture which is grasped within the hook is retracted into the sheath along with the hook rod creating a snug fit between the inner wall of the sheath and the hook rod.

An alternative embodiment of this invention utilizes a thin hollow tubular hook rod slidably mounted in a sheath. The hook rod can thus be used to introduce gas into or out of an abdominal or thoracic cavity. A valve mounted to the proximal end of the hook rod controls the flow of gas through the hook rod, into or out of the cavity.

This invention overcomes the disadvantages of the prior art Semm Needle by using a hypodermic type small diameter penetrating point, thereby reducing the amount of force needed to penetrate tissue. The reduced force results in increased control during, and immediately upon, penetration. Moreover, the invention contemplates using a hook rod with a round or blunt tip. Thus, once the device has penetrated the peritoneum, the hook rod is extended beyond the penetrating point, such that the tip is exposed, minimizing the potential for damage resulting from inadvertent tissue or organ perforation.

In addition, upon grasping a suture, the hook rod is retracted into the sheath, positively securing the suture between the hook rod and the inner wall of the sheath. Lastly, this invention utilizes a smooth wall sheath to minimize the damage to surrounding tissue upon removing the device from the abdominal or thoracic cavity.

This invention also has an advantage, over the prior art Veress needle, of having suture externalization capability. Veress needles provide only for insufflating an abdominal cavity. The present invention provides for insufflation and suture externalization in a single instrument. Thus, the invention can be used to insufflate an abdominal or thoracic cavity in the early stages of the surgical procedure, retract sutures and organs during the procedure, and return the cavity to ambient pressure at the end of the procedure.

BRIEF DESCRIPTION OF THE DRAWINGS

A more complete appreciation of this invention, and many of the attendant advantages thereof, will be readily apparent as the same becomes better understood by reference to the following detailed description, when considered in conjunction with the accompanying drawings, in which like reference numerals indicate the same or similar components, wherein:

FIG. 1 is a perspective view of a preferred embodiment of the percutaneous suture externalizer device of the present invention shown in its extended position grasping a suture within an abdominal cavity;

FIG. 2 is an elevation view, partially in cross section and partially broken away, of the percutaneous suture externalizer shown in FIG. 1 with the hook rod in its extended or first position;

FIG. 3 is an elevation view, partially in cross section and partially broken away, of the percutaneous suture externalizer shown in FIG. 1 with the hook rod in its retracted or second position;

FIG. 8 is a perspective view of an alternative embodiment of the percutaneous suture externalizer device of the present invention shown in its extended position, mounted in a stabilizer, grasping a suture within an abdominal cavity;

FIG. 9 is an enlarged front view of the distal end of the percutaneous suture externalizer device shown in FIG. 8 with the hook rod in its extended position;

FIG. 10 is a cross sectional side view of the distal end of the hook as shown in FIG. 9;

FIG. 11 is an enlarged front view, similar to FIG. 9, with the hook rod in a partially retracted position with a suture portion grasped therein;

FIG. 12 is a cross sectional view of the sheath and hook rod taken along line 12—12 in FIG. 11; and FIG. 13 is an elevation view, partially in cross section and partially broken away, of the percutaneous suture externalizer device shown in FIG. 8 with the hook rod in its extended position.

DETAILED DESCRIPTION OF THE PREFERRED EMBODIMENTS

Figure 4:
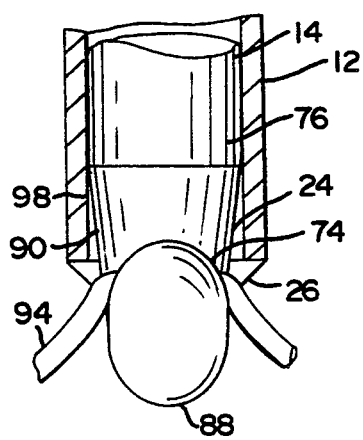
FIG. 4 is an enlarged partial cross sectional view of the distal end of the externalizer device with the hook rod in its extended position with a suture grasped within the hook.

Referring generally to FIG. 1, there is shown a first preferred embodiment of a percutaneous suture externalizer device 10, constructed in accordance with the invention, which includes a sheath 12, a hook rod 14, a housing 16 and a retracting knob 18.

Referring generally to FIGS. 2 and 3, the sheath 12 includes a thin wall hollow tube 13 having an open distal end portion 20 and an open proximal end portion 22 defining a bore 24. The sheath is preferably about two (2) millimeters in diameter. The distal end portion 20 of sheath 12 terminates in a hypodermic type penetrating point 26. The proximal end portion 22 of sheath 12 terminates in a sheath block 28. Sheath block 28 has a generally rectangular or cylindrical shape and has a bore 30 of substantially the same diameter as the diameter of bore 24 defined by sheath 12. Bore 24 is contiguous with the bore 30 of sheath block 28. Sheath 12 and sheath block 28 can be a single piece manufacture or a multiple piece assembly and are preferably fabricated from a surgical quality material such as stainless steel or the like.

The housing 16 has a proximal end portion 39 and a distal end portion 32. Housing 16 is preferably fabricated in two halves from a suitable plastic material. Internally, housing 16 is formed with a proximal lip 36 and a distal lip 38. Proximal lip 36 is located in the proximal end portion 39 of housing 16 and defines a proximal surface 40 and a distal surface 42. Distal lip 38 is located in the distal end portion 32 of housing 16 and defines a proximal surface 48 and a distal surface 50. A bore 51 is formed in proximal end portion 39 having a rectangular cross section. In an alternative construction of suture externalizer 10 (not shown), bore 51 has a circular cross section and a key way is formed in proximal end portion 39, parallel to and contiguous with bore 51.

Retracting knob 18 is formed so as to define a generally mushroom shaped proximal portion 54, a stem portion 56, and a knob shaft 58. Retracting knob 18 is preferably fabricated from a suitable plastic material. Stem portion 56 and knob shaft 58 have a generally rectangular cross section. Stem portion 56 has a larger cross section than knob shaft 58. In an alternative construction of suture externalizer 10 (not shown), knob shaft 58 has a circular cross section, and a projection is formed, longitudinally, along knob shaft 58. The distal portion 66 of knob shaft 58 has a recess 59 extending longitudinally some distance along the knob shaft 58. Recess 59 defines a knob ring 60 at the distal end 68 of knob shaft 58.

A ridge 70 is formed at the interface between proximal portion 54 and stem portion 56. The ridge 70 constitutes a lip or thumb rest. Recesses or projections 72 are preferably longitudinally formed along stem portion 56 which align with an indicator 78 located on proximal portion 54 of retracting knob 18.

Hook rod 14 is a thin rod having a proximal portion 75 and a distal portion 76. The diameter of the hook rod 14 is slightly smaller than the diameter of the bore 24 of sheath 12. The distal portion 76 of hook rod 14 has a smaller diameter than proximal portion 75. As exemplified in FIGS. 4–5, distal portion 76 is tapered inwardly and distally at 90. Alternative constructions, not shown, for reducing the diameter of distal portion 76 may include a smaller diameter distal portion 76 that is transitioned by shoulders to proximal portion 75. The tip 88 of hook rod 14 is round or blunt. A hook 74, proportioned to accommodate a suture 94, is located at the distal portion 76. The hook rod 14 is preferably fabricated from a suitable surgical quality material such as stainless steel or the like.

Sheath block 28 and the proximal end portion 22 of sheath 12 are fixedly mounted in housing 16 such that the distal end portion 20 of sheath 12 extends distally beyond distal end portion 32 of housing 16. Sheath block 28 is located within housing 16 such that the distal surface 50 of lip 38 abuts against sheath block 28. The housing 16 forms an enclosure 52 around sheath block 28.

Hook rod 14 is fixedly mounted within retracting knob 18, such that the distal portion 76 of hook rod 14 extends beyond distal end 68 of knob shaft 58, and hook 74 is in alignment with the recesses or projections 72 formed along stem portion 56 and the indicator 78 located on proximal portion 54.

The retracting knob 18 and hook rod 14 are slidably mounted within housing 16, sheath block 28 and sheath 12, such that the proximal end portion 62 of knob shaft 58 is slidable within bore 51. In a first or extended position, hook 74 extends beyond the penetrating point 26 of sheath 12. A coil spring 44 is disposed within housing 16 between the distal surface 42 of lip 36 and the knob ring 60. Coil spring 44 biases hook rod 14 into its extended position. Movement of hook rod 14 beyond the extended position is limited by knob ring 60 abutting against surface 48 of lip 38.

In the second or retracted position, hook 74 retracts within sheath 12. The retracted position is limited by the length of the fully compressed coil spring 44 in contact with distal surface 42 of lip 36, and knob ring 60.

In a construction of suture externalizer 10, wherein knob shaft 58 and bore 51 have a rectangular cross section, retracting knob 18 and hook rod 14 are not rotatable relative to the housing 16 due to the shape of the knob shaft 58 fitting within bore 51. In an alternative construction (not shown) wherein knob shaft 58 and bore 51 have a circular cross section, the projection on knob shaft 58, extends into the key way formed in bore 51 to prevent rotation of the retracting knob 18 and hook rod 14 relative to housing 16. This prevents misalignment of hook 74 relative to penetrating point 26.

Figure 5:
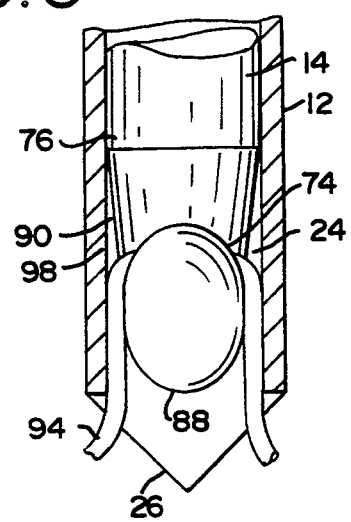
FIG. 5 is an enlarged partial cross sectional view of the distal end of the externalizer device with the hook rod in its retracted position with a suture grasped within the hook.
Figure 6:
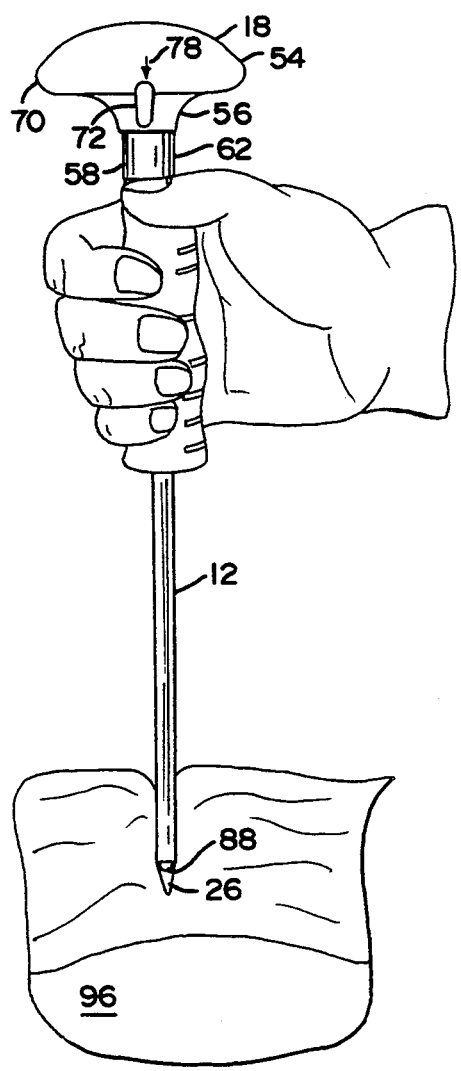
FIG. 6 is a perspective view of the percutaneous suture externalizer, with the hook rod being forced into its retracted position by tissue resistance while being inserted through the abdominal wall.
Figure 7:
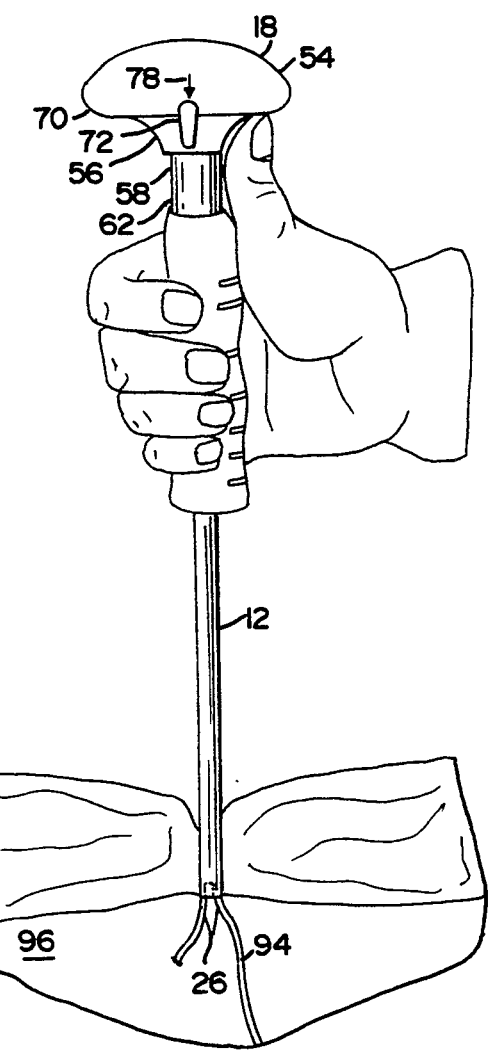
FIG. 7 is a perspective view of the percutaneous suture externalizer, with the hook rod being manually moved to its retracted position, and having a suture grasped therein as it is being externalized.

In operation, referring generally to FIGS. 6 and 7, the housing 16 is grasped such that maximum control is obtained during insertion. A downward pressure sufficient to insert the percutaneous suture externalizer device 10 into the abdominal or thoracic cavity 96 is applied. Once inserted, a suture 94 located using, for example, laparoscopic means, and is grasped within the hook 74. The orientation of hook 74 is externally identifiable by the recesses or projections 72 located on stem portion 56 or indicator 78 located on retracting knob 18. A suture is then grasped in the hook 74, and an upward force is applied to the ridge 70 of retracting knob 18, moving hook rod 14 into its retracted position. Referring generally to FIGS. 4, 5 and 7, the suture portion 94 so grasped along with hook rod 14, when in the retracted position, creates a snug fit between hook rod 14 and the inner wall 98 of sheath 12. This snug fit positively secures suture portion 94 between inner wall 98 and hook rod 14. The suture portion 94 can then be externalized from the abdominal cavity 96.

Referring to FIGS. 8-13, there is shown a second preferred embodiment of a percutaneous suture externalizer 10' of this invention. Except as shown and described, percutaneous suture externalizer 10' is similar to percutaneous suture externalizer 10, and elements designated by primed numbers in FIGS. 8-13 correspond to elements designated by the same unprimed numbers in FIGS. 1-7. Percutaneous suture externalizer device 10' includes a sheath 12', a hook rod 104, a housing 16' and a retracting knob 108.

Referring generally to FIGS. 8, 10 and 13, sheath 12' includes a thin wall hollow tube 13' having an open distal end portion 20' and an open proximal end portion 22' defining a bore 24'. Sheath 12' is preferably about two (2) millimeters in diameter. The distal end portion 20' of sheath 12' terminates in a hypodermic type penetrating point 26'. The proximal end portion 22' of sheath 12' terminates in a sheath block 28'. Sheath block 28' has a generally rectangular or cylindrical shape and has a bore 30' of substantially the same diameter as the diameter of bore 24'. Bore 24' is contiguous with bore 30' of the sheath block 28'. Sheath 12' and sheath block 28' can be a single piece manufacture or a multiple piece assembly, and are preferably fabricated from a surgical quality material such as stainless steel or the like.

Housing 16' has a proximal end portion 39' and a distal end portion 32'. Housing 16' is preferably fabricated in two halves from a suitable plastic material. Internally, housing 16' is formed with a proximal lip 36' and a distal lip 38'. Lip 36' is located in the proximal end portion 39' of housing 16' and defines a proximal surface 40' and a distal surface 42'. Lip 38' is located in the distal end portion 32' of housing 16' and defines a proximal surface 48' and a distal surface 50'. A bore 51' is formed in proximal end portion 39' having a rectangular cross section. In an alternative construction of suture externalizer 10' (not shown), bore 51' has a circular cross section, and a key way is formed in proximal end portion 39', parallel to and contiguous with bore 51'.

Retracting knob 108 is formed so as to define a generally mushroom shaped proximal portion 154, a stem portion 156, and a knob shaft 158. Retracting knob 108 is preferably fabricated from a suitable plastic material. Stem portion 156 and knob shaft 158 have a generally rectangular cross section. Stem portion 156 has a larger cross section than knob shaft 158. In an alternative construction of suture externalizer 10' (not shown), knob shaft 158 has a circular cross section, and a projection is formed, longitudinally, along the knob shaft 158. The distal portion 166 of knob shaft 158 has a recess 159 extending longitudinally some distance along knob shaft 158. Recess 159 defines a knob ring 160 at the distal end 168 of knob shaft 158.

A ridge 70' is formed at the interface between proximal portion 154 and stem portion 156. Ridge 70' constitutes a lip or thumb rest. Recesses or projections 72' are preferably longitudinally formed along stem portion 156 and align with an indicator 78' located on proximal portion 154 of retracting knob 108.

Hook rod 104 is a thin hollow tubular rod having an open proximal portion 175 and an open distal portion 176 defining a bore 191. The outside diameter of hook rod 104 is slightly smaller than the diameter of bore 24'. A hook 174, proportioned to accommodate a suture 94', is located at and extends beyond distal portion 176 of hook rod 104. The hook 174 is fixedly mounted to inner wall 192 of hook rod 104. The shank 194 of hook 174 tapers inwardly and distally from mounting location 195 to tip 188. Tip 188 is round or blunt. A valve 196, or other gas flow control device, is mounted to the proximal portion 175 of hook rod 104. Hook rod 104 and hook 174 are preferably fabricated from a suitable surgical quality material such as stainless steel or the like.

Sheath block 28' and proximal end portion 22' of sheath 12' are fixedly mounted in housing 16' such that the distal end portion 20' of sheath 12' extends distally beyond the distal end portion 32' of housing 16'. Sheath block 28' is located within housing 16' such that the distal surface 50' of lip 38' abuts against sheath block 28'. Housing 16' forms an enclosure 52' around sheath block 28'.

The intermediate portion 198 of hook rod 104 is fixedly mounted within retracting knob 108, such that the distal portion 176 of hook rod 104 extends beyond the distal end 168 of knob shaft 158, and the proximal portion 175 of hook rod 104 extends beyond the proximal portion 154 of retracting knob 108. Hook rod 104 is mounted within retracting knob 108 such that the hook 174 is in alignment with the recesses or projections 72' formed along stem portion 156 and the indicator 78' located on proximal portion 154.

The retracting knob 108 and hook rod 104 are slidably mounted within housing 16', sheath block 28' and sheath 12, such that the proximal end portion 162 of knob shaft 158 is slidable within bore 51'. In a first or extended position, hook 174 extends beyond penetrating point 26' of sheath 12'. A coil spring 44' is disposed within housing 16' between the distal surface 42' of lip 36' and knob ring 160. Coil spring 44' biases hook rod 104 into the extended position. Knob ring 160 abuts against surface 48' of lip 38' to limit movement of hook rod 104 beyond its extended position.

In its retracted position, hook 174 retracts within sheath 12'. The fully retracted position is limited by the length of the fully compressed coil spring 44' in contact with surface 42' of lip 36', and knob ring 160.

In a construction of suture externalizer 10', wherein knob shaft 158 and bore 51' have a rectangular cross section, retracting knob 108 and hook rod 104 are not rotatable relative to the housing 16' due to the shape of the knob shaft 158 fitting within bore 51'. In an alternative construction (not shown) wherein knob shaft 158 has a circular cross section, the projection on knob shaft 158, extends into the key way in bore 51' to prevent rotation of the retracting knob 108 and hook rod 104 relative to housing 16'. This prevents misalignment of hook 174 relative to penetrating point 26'.

In operation, referring generally to FIG. 8, the housing 16' is grasped such that maximum control is obtained during insertion. A downward pressure sufficient to insert the percutaneous suture externalizer device 10' into the abdominal or thoracic cavity 96' is applied. Once inserted, a suture 94' is located using, for example, laparoscopic means, and is grasped within the hook 174. The orientation of hook 174 is externally identifiable by the recesses or projections 72' located on stem portion 156 or indicator 78'. A suture 94' is then grasped in hook 174, and an upward force is applied to the ridge 70' of retracting knob 108, moving hook rod 104 into its retracted position. The suture portion 94' so grasped along with hook rod 104, when in the retracted position, creates a snug fit between hook rod 104 and inner wall 98' of sheath 12'. This snug fit positively secures the suture portion 94' between inner wall 98' and hook rod 104 in a similar manner as discussed above with respect to the externalizer 10. The suture portion 94' can then be externalized from the abdominal or thoracic cavity 96'.

Alternatively, the suture externalizer 10' can be used to insufflate the abdominal or thoracic cavity 96'. In operation similar to suture externalization, the suture externalizer 10' is inserted into the cavity 96'. Hook rod 104 is allowed to bias to its extended position, and valve 196, or other gas flow control device, is opened, and gas or ambient air is introduced into cavity 96'. Once the desired pressure is achieved, valve 196 can be closed or set to regulate the internal pressure of the cavity 96'. The suture externalizer 10' can be used to externalize or retract a suture 94' or operate as an insufflation device, or perform both functions during a surgical procedure.

Either embodiment of the suture externalizer 10, 10' can be stabilized using a stabilizer 80' of well known construction as shown in FIG. 8. Stabilizer 80' consists of a main body 82' and a cap 84'. Main body 82' has legs 86' which support stabilizer 80' and maintain suture externalizer 10' vertical relative to the abdomen 88'. Cap 84' and main body 82' have threads (not shown) which when screwed together, engage a ferrule type locking device (not shown). The ferrule clamps onto sheath 12' to allow the suture externalizer 10' to be set to a desired depth in abdominal or thoracic cavity 96'. This arrangement allows for retracting a portion of a suture 94', or regulating cavity 96' pressure without continuous manual operation of the suture externalizer 10'.

From the foregoing it will be observed that numerous modifications and corrections can be effected without departing from the true spirit and scope of the novel concepts of the present invention. It will be understood that no limitation with respect to the specific embodiments illustrated herein is intended or should be inferred. It is, of course, intended to cover by the appended claims all such modifications as fall within the scope of the claims.

What is claimed is:

1. A suture externalizer comprising:

(a) a sheath having a proximal end portion and a distal end portion, said distal end portion having a sharp penetrating point;
   (b) a hook rod having a proximal end portion and a distal end portion, said distal end portion having grasping means for grasping a suture;
   (c) a housing having a proximal end and a distal end, said proximal end portion of said sheath being positioned in said housing and extending from said distal end thereof;
   (d) a retracting knob having a proximal end portion and a distal end portion, said proximal end portion of said hook rod being fixedly mounted to said distal end portion of said retracting knob, said distal end portion of said retracting knob being slidably received within said housing;
   (e) said hook rod being slidably received within said sheath for moving between a first position, wherein said grasping means extends beyond said penetrating point for grasping a portion of a suture and protecting said penetrating point, and a second position, wherein said grasping means and at least a portion of a suture retract within said sheath; and
   (f) biasing means for biasing said hook rod into its first position, said biasing means being contained within said housing.

2. A suture externalizer as set forth in claim 1 wherein said distal end portion of said hook rod being inwardly distally tapered.

3. A suture externalizer as set forth in claim 1, further including a gap between said hook rod and said sheath for securing a portion of said suture therebetween when said hook rod is in said second position.

4. A suture externalizer as set forth in claim 1 wherein said grasping means comprises a hook disposed at the distal end portion of said hook rod, said hook being proportioned to accept a portion of a suture grasped therein.

5. A suture externalizer as set forth in claim 1 wherein said biasing means comprises a coil spring.

6. A suture externalizer as set forth in claim 1 wherein said retracting knob contains orientation means aligned with said grasping means.

7. A suture externalizer as set forth in claim 1 wherein said retracting knob contains orientation means aligned with said grasping means.

8. A suture externalizer comprising:

(a) a sheath having a proximal end portion and a distal end portion, said distal end portion having a shape penetrating point;
   (b) a hook rod defining a bore extending therethrough, said hook rod having an open proximal end portion, an intermediate portion and an open distal end portion, said distal end portion having a grasping means for grasping a suture;
   (c) said hook rod being slidably received within said sheath for moving between a first position, wherein said grasping means extends beyond said penetrating point for grasping a portion of a suture, and a second position, wherein said grasping means and at least a portion of a suture retract within said sheath; and
   (d) means for controlling flow of a gas through said bore in said hook rod.

9. A suture externalizer as set forth in claim 8 further comprising biasing means for biasing said hook rod into its first position.

10. A suture externalizer as set forth in claim 8 wherein said distal end portion of said hook rod being inwardly distally tapered.

11. A suture externalizer as set forth in claim 8, further including a gap between said hook rod and said sheath for securing a portion of said suture therebetween when said hook rod is in said second position.

12. A suture externalizer as set forth in claim 8 wherein said grasping means comprises a hook disposed at the distal end portion of said hook rod, said hook being proportioned to accept a portion of a suture grasped therein.

13. A suture externalizer as set forth in claim 9 further including a housing having a proximal end and a distal end, said biasing means being contained within said housing, and said proximal end portion of said sheath being positioned in said housing and extending from said distal end of said housing.

14. A suture externalizer as set forth in claim 13 wherein said biasing means comprises a coil spring.

15. A suture externalizer as set forth in claim 14 further including a retracting knob, said retracting knob having a proximal end portion and a distal end portion, said intermediate portion of said hook rod being fixedly mounted in said retracting knob, said retracting knob being slidably received within said housing, and said retracting knob having a recess for receipt of said coil spring.

16. A suture externalizer as set forth in claim 15 wherein said retracting knob contains orientation means aligned with said grasping means.

17. A suture externalizer as set forth in claim 8 wherein said means for controlling flow of gas through said bore in said hook rod comprises a valve mounted to the proximal end portion of said hook rod.

18. A suture externalizer as set forth in claim 1 further including stabilizing means associated with said sheath for maintaining said suture externalizer in a predetermined position.

19. A suture externalizer as set forth in claim 8 further including stabilizing means associated with said sheath for maintaining said suture externalizer in a predetermined position.

* * * * *